US012508148B2

(12) United States Patent
Xiang et al.

(10) Patent No.: US 12,508,148 B2
(45) Date of Patent: Dec. 30, 2025

(54) EASILY FORMED ARM EXTERNAL FIXING BRACE

(71) Applicant: WUHAN XUNSHU TECHNOLOGY CO., LTD., Hubei (CN)

(72) Inventors: Guxi Xiang, Hubei (CN); Zhiwei Ouyang, Hubei (CN)

(73) Assignee: Wuhan Xunshu Technology Co., LTD, Hubei (CN)

( * ) Notice: Subject to any disclaimer, the term of this patent is extended or adjusted under 35 U.S.C. 154(b) by 742 days.

(21) Appl. No.: 17/430,337

(22) PCT Filed: Feb. 12, 2019

(86) PCT No.: PCT/CN2019/074867

§ 371 (c)(1),
(2) Date: Aug. 12, 2021

(87) PCT Pub. No.: WO2020/163994

PCT Pub. Date: Aug. 20, 2020

(65) Prior Publication Data

US 2022/0125616 A1 Apr. 28, 2022

(51) Int. Cl.
*A61F 5/058* (2006.01)
*A61L 15/12* (2006.01)

(52) U.S. Cl.
CPC ........ *A61F 5/05858* (2013.01); *A61L 15/125* (2013.01)

(58) Field of Classification Search
CPC .... A61F 5/00; A61F 5/01; A61F 5/058; A61F 5/05841–05875; A61F 5/0102;
(Continued)

(56) References Cited

U.S. PATENT DOCUMENTS 1,277,595 A * 9/1918 Jaffe ........................ A44B 1/34 24/108
4,658,441 A * 4/1987 Smith .................. A41D 13/087 2/21
(Continued)

FOREIGN PATENT DOCUMENTS

DE 2638527 A1 * 3/1977 ............... A44B 1/04
KR 101490874 B1 * 2/2015 ............... A44B 1/06
(Continued)

*Primary Examiner* — Camtu T Nguyen
(74) *Attorney, Agent, or Firm* — ASHLEY LAW FIRM P.C.; Stephen S. Ashley, Jr.

(57) ABSTRACT

An arm external fixing brace (10), characterized by a thickness (H) of an edge of a mesh panel (12) thereof being greater than a thickness (B) of a central location. Selectively, raw materials of the mesh panel (12) being, according to weight: 60-78% PCL; 20-38% EVA; 2-20% inorganic filler; a thickness of an edge of a large ventilation hole of the mesh panel (12) being less than a thickness between the centers of two adjacent large ventilation holes; multiple fastening substrates (300) being pre-embedded at adjacent horizontal edge locations of the mesh panel (12); two wings of a fastening substrate (300) being provided with side holes (305), two sides of a middle part of a fastening substrate (300) being provided with grooves (302, 303) having symmetrical structures, the middle part of a fastening substrate (300) being provided with a middle hole (304), and a non-return surface (301) being provided at two sides of a circumference of the middle hole (304) inside the grooves (302, 303); two sides of a thumb hole (15) of the mesh panel (12) being tapered surfaces having symmetrical structures. The arm external fixing brace has few components, but simultaneously can prevent adhesion during a molding process so as to facilitate removal from a mold, make clinical operation convenient, and be comfortable to wear, metrics which were previously in conflict with one another.

10 Claims, 4 Drawing Sheets

(58) Field of Classification Search

CPC ...... A61F 5/0104; A61F 5/0118; A61F 5/013; A61F 5/05825; A61F 5/04; A61F 5/05; A61F 5/05858–05875; A61F 5/10; A61F 13/04; A61F 2005/0186; A61F 2007/0037; A61F 2007/0038; A61F 2007/0036; A61L 15/07–14; A41D 13/08–088; A41D 19/01588; A41D 19/0013; A41D 19/0017; A44B 1/34

See application file for complete search history.

(56) References Cited

U.S. PATENT DOCUMENTS

| | | | | | |
|---|---|---|---|---|---|
| 5,515,870 | A * | 5/1996 | Zilber | A61F 5/50 | 128/880 |
| 6,093,161 | A * | 7/2000 | Vlaeyen | A61F 5/05 | 602/5 |
| 6,200,286 | B1 * | 3/2001 | Zamani | A61F 5/0118 | 602/20 |
| 7,314,457 | B2 * | 1/2008 | Reaux | A61F 13/04 | 602/61 |
| 8,303,527 | B2 * | 11/2012 | Joseph | A61F 5/0111 | 602/8 |
| 8,458,817 | B1 * | 6/2013 | Babb | A41D 19/0013 | 2/163 |
| 8,545,422 | B2 * | 10/2013 | Watson | A61F 5/058 | 602/5 |
| 9,861,167 | B2 * | 1/2018 | Shirai | A44B 1/34 | |
| 2004/0024337 | A1 * | 2/2004 | Tseng | A61F 13/04 | 602/6 |
| 2004/0210177 | A1 * | 10/2004 | Grim | A61F 5/01 | 602/8 |
| 2005/0165338 | A1 * | 7/2005 | Iglesias | A61F 5/0111 | 602/21 |
| 2006/0155226 | A1 * | 7/2006 | Grim | A61F 13/041 | 602/8 |
| 2010/0036300 | A1 * | 2/2010 | Sheehan | A61F 5/05825 | 602/7 |
| 2013/0317788 | A1 * | 11/2013 | Summit | G06F 30/00 | 703/1 |
| 2015/0250636 | A1 * | 9/2015 | Darcey | A61F 5/058 | 602/5 |
| 2017/0216078 | A1 * | 8/2017 | Rivlin | A61F 5/05866 | |
| 2019/0040884 | A1 | 2/2019 | He | | |
| 2020/0009288 | A1 * | 1/2020 | Geremtzes | A61L 15/12 | |

FOREIGN PATENT DOCUMENTS

| | | | | | |
|---|---|---|---|---|---|
| WO | WO-2014191918 | A1 * | 12/2014 | A44B 1/34 | |
| WO | WO-2016026775 | A1 * | 2/2016 | A61F 5/05841 | |

* cited by examiner

EASILY FORMED ARM EXTERNAL FIXING BRACE

TECHNICAL FIELD

The present invention relates to an arm external fixing brace, in particular to an easily formed arm external fixing brace, belonging to the technical field of fracture external fixation.

PRIOR ART

In prior art, a medical fixing brace which can most closely contact a skin of an arm is formed by a 3D printing. However, it has obvious disadvantages. The brace, not a single piece of product, has to have at least two parts to be combined together. After the brace is put on the arm, its tightness can no longer be adjusted, and there is no connecting means to regulate the tightness. Moreover, the brace has several curved surfaces, forming a three-dimensional structure, not a flat blank, so it is not convenient for packaging, transporting, storing and using. The brace blank can no longer be further stretched in clinical use, i.e., cannot be reformed arbitrarily when it is used in clinic. The brace itself is hard, not able to make any desired plastic deformation when immersing in hot water.

In prior art, a medical fixing brace for the most convenient packaging, transporting, storing and using is a mesh plate with a uniform thickness. In its clinical use, however, as some portions of human body are fat or thin, the fixing brace cannot fully contact the injured arm, even if the fixing brace itself is flexible.

In prior art, an undersurface of the two terminals of a connecting means of the arm fixing brace is not flush with the skin contacting surface of the arm fixing device itself, an edge for a containing hole for assembling two terminals of the connecting means could result in a local skin damage, such as a poor blood supply or even a skin ulceration, which has been ignored for a long time.

In prior art, a thickness around a thumb hole of the arm fixing brace is constant, no gradual thickness variation at all, leading a poor wearing comfort for patient. If a thumb holding cylinder is put into the thumb hole, the patient's wearing amenity becomes worse, easily causing a poor local skin blood supplying, skin ulceration, and other possible damages.

CN102430156A discloses a mesh plate comprising by weight: 30-50% of PCL; 0-20% of EVA; 35-50% of inorganic filler (e.g., talc powder, calcium carbonate, silicate); 1-5% of colorant; and 0.1-1.0% of crosslinking agent.

CN201710945969.X discloses a mesh plate comprising by weight: 40-75% of PCL; 0% of EVA; 18-50% of filler (such as PP, PC, grafted PP); 7-10% of auxiliary materials (such as talc, calcium carbonate, silicate); and 0.1-1.0% of crosslinking agent.

In prior art, the arm external fixing brace is made from many raw components, with a complex ingredient mixing process, a complex manufacturing process, a plurality of control parameters, and a high production cost.

SUMMARY OF THE INVENTION

The object of the present invention is to provide an arm external fixing brace, which is molded integrally by a one-time injection, does not need any cutting and never adheres to itself during a clinical use, and makes is possible for doctors to perform a simple and fast operation.

Another object of the present invention is to provide a composite material which has a simpler formula, is easy for a product prototype to go out from its mold after an injection molding, and is not adhesive in processing, so that a process for using the composite material is simplified, a cost for making the fixing brace is greatly reduced, and an amenity for patients to wear the same is greatly improved.

Therefore, according to the first aspect of the present invention, there is provided an arm external fixing brace, wherein a thickness of edges of a mesh plate is greater than that of a central portion thereof.

Preferably, a thickness of an edge of a large air hole of the mesh plate is less than a thickness at a bridging portion between two adjacent large air holes.

Preferably, a plurality of snap fastener substrates are embedded near transverse edges of the mesh plate.

Preferably, two wings of the snap fastener substrate are each provided with a side hole, the two side surfaces of a central portion of the snap fastener substrate are symmetrically provided with concaves, the central portion of the snap fastener substrate is provided with a central hole, and check surfaces are arranged on both side surfaces of the snap fastener substrate and around the central holes passing through the two concaves.

Preferably, the concave is a non-circular structure.

Preferably, the non-circular structure is oblong, square, D-shaped, or at least a structure with a straight edge.

Preferably, the more far away from a center of the thumb hole, the greater thickness of an edge of a thumb hole of the mesh plate.

Preferably, both side surfaces of the thumb hole of the mesh plate are conical surfaces with a symmetrical structure.

According to the second aspect of the present invention, there is provided a thumb holding accessory, wherein it has a base and a thumb holding cylinder, and the base has a frustum and an undersurface; an upper wall of the thumb holding cylinder is provided with at least one longitudinal slit; a side wall of the thumb holding cylinder is provided with at least one air hole; and a ring with a reduced thickness connects the thumb holding cylinder to the base.

Preferably, the thumb holding accessory is of a large size, a medium size, or a small size; and preferably, a height thereof is 56 mm, 64 mm or 72 mm, respectively; a length tolerance thereof is ±7 mm, a thickness tolerance thereof is ±2 mm; the base is oblong, 72 mm long and 56 mm wide; and a base thickness is preferably 1 mm.

According to the third aspect of the present invention, the arm external fixing brace comprises 60-78 weight % of PCL (polycaprolactone); 20-38 weight % of EVA (ethylene vinyl acetate copolymer); and 2-20 weight % of inorganic filler.

Preferably, the inorganic filler is talcum powder, calcium carbonate or silicate.

According to the fourth aspect of the present invention, there is provided a process for making an arm external fixing brace, wherein it is a method carried out by a low temperature, high pressure, slow feeding, and multi-point injection molding.

Preferably, its sol temperature is set at 80-160° C.; its injection pressure is in a range of 40-150 MPa; and an injecting rate is in a range of 2-25 g/s.

According to the fifth aspect of the present invention, there is provided a method for using an arm external fixing brace, wherein a thumb holding cylinder is inserted into a thumb hole of a mesh plate, so that a frustum surface of a base of a thumb holding accessory abuts a cone surface of a thumb hole edge of the mesh plate, thus making a gap between the base and the thumb hole edge disappear, so that a base undersurface of the thumb holding accessory is flush with a skin contacting surface of the mesh plate in clinical use.

According to the present invention, a mesh plate of the arm external fixing brace is no longer with a content thickness everywhere, but its thickness in different areas is variated to correspond to a human anatomical structure, which enhances a wearing amenity and fitness to a patient's skin, but a function of the mesh plate is not sacrificed.

According to the present invention, an inner edge of the thumb hole of the mesh plate of the arm external fixing brace has a thickness gradient, i.e., the inner edge of the thumb hole becomes thinner gradually towards a center of the thumb hole.

According to the present invention, the mesh plate of the arm external fixing brace is further provided a bottom plug for a snap fastener, which not only make the snap fastener stronger in use, but also covers a hole bottom of the snap fastener substrate. An unexpected effect is to make a contacting surface between the mesh plate and the user's skin smooth, preventing any damage from a local skin blood supply and a skin ulceration caused by the hole bottom edge of the snap fastener substrate.

According to the present invention, the mesh plate of the arm external fixing brace can be used both for a left arm and for a right arm, making its clinical operation simple, which facilitates to reduce kinds of product models, increase amount for each kind of product, and reduce its cost. According to the present invention, the mesh plate of the arm external fixing brace has less raw material ingredients, simple and convenient preparation of components, less control parameters, simple manufacturing process and low production cost.

BRIEF DESCRIPTION OF THE ACCOMPANYING DRAWINGS

Figure 1A:
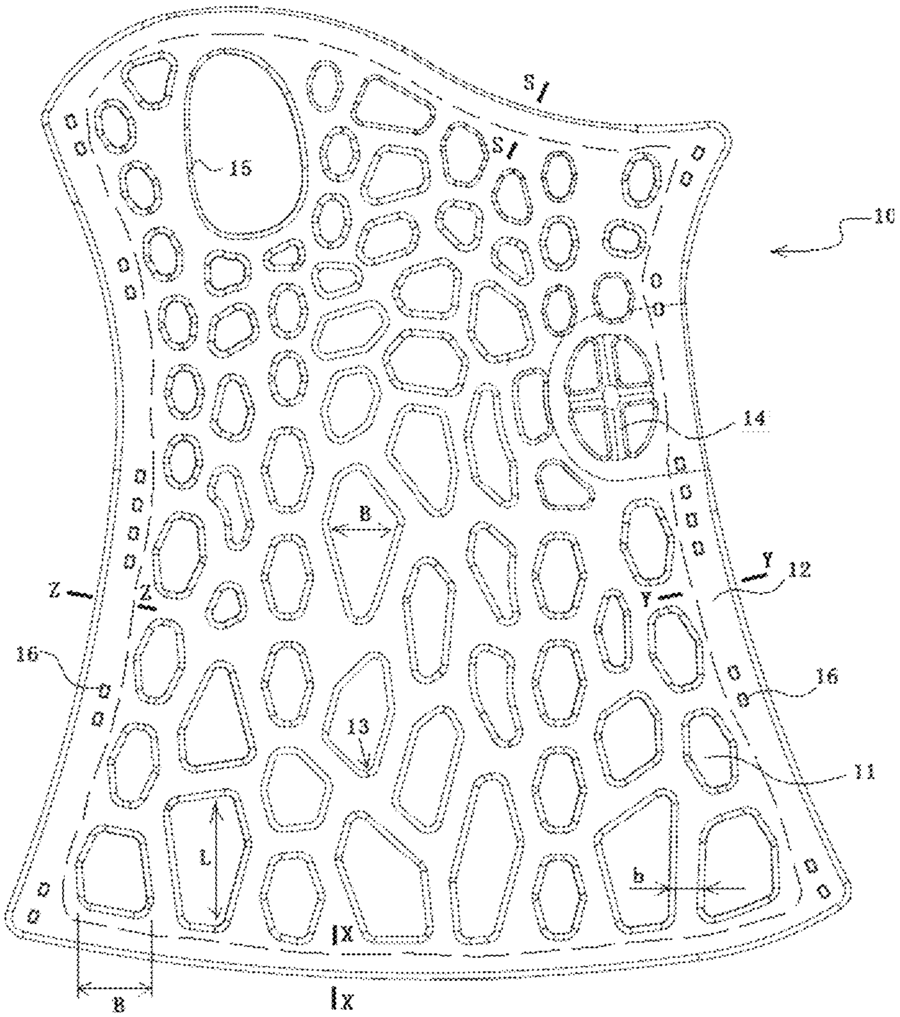
FIG. 1A is a schematic view of a blank of an arm external fixing brace according to an embodiment of the present invention.
Figure 2A:
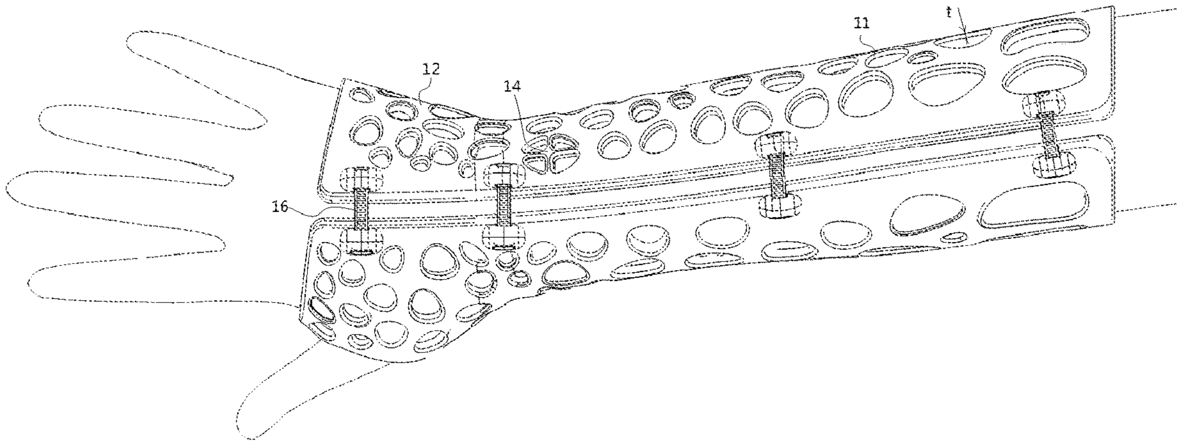
Figure 2B:
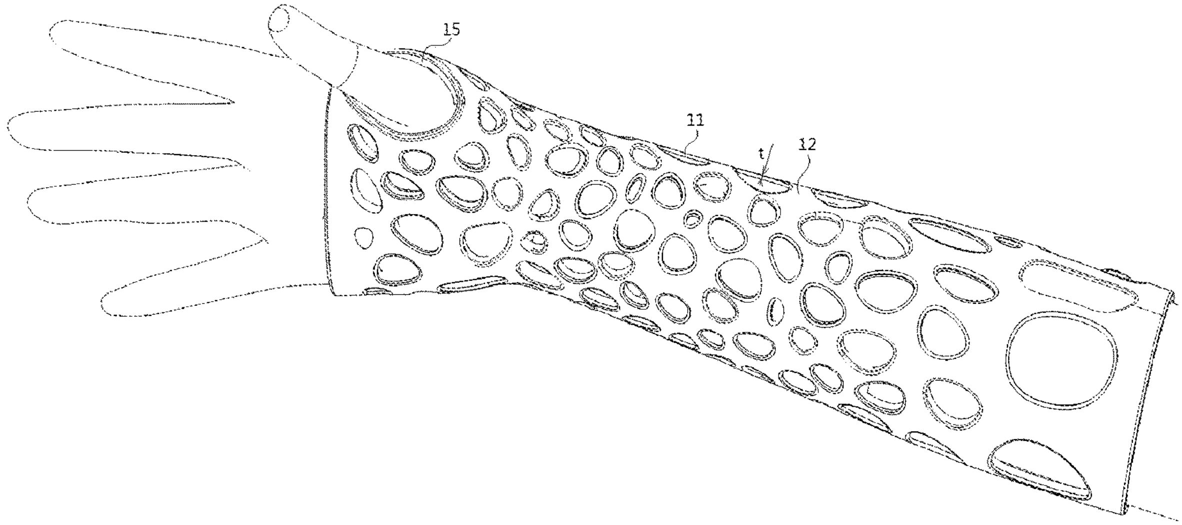

FIGS. 2*a*-2*b* are schematic views of a usage of the embodiment as shown in FIG. 1A.

FIGS. 3*a*-3*e* are schematic views of some snap fasteners of connecting means of the arm external fixing brace according to the present invention.

Figure 4:
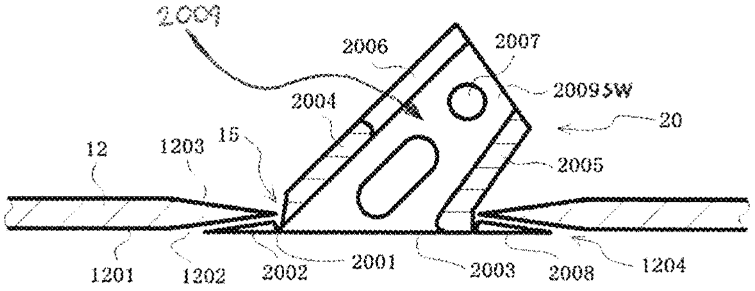

FIG. 4 is a schematic view of a thumb holding cylinder according to the present invention.

Figure 5:
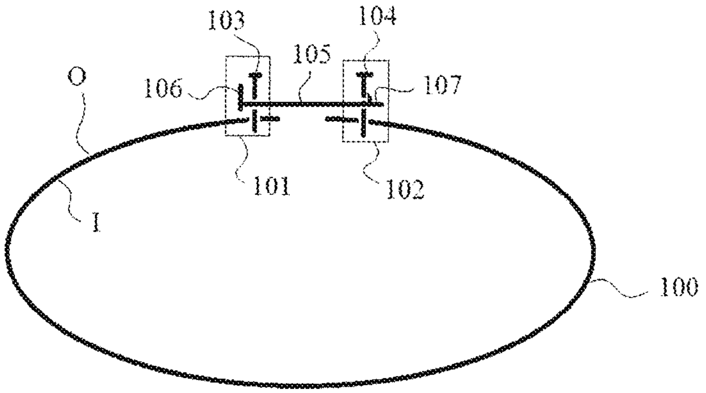

FIG. 5 is a schematic diagram of a snap fastener of the connecting means of the arm external fixing brace according to an embodiment of the present invention.

Figure 6:
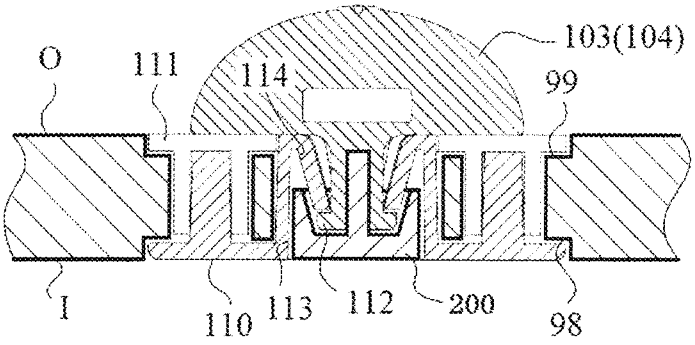

FIG. 6 is an assembled status of the snap fastener as shown in FIG. 5.

Figure 7A:
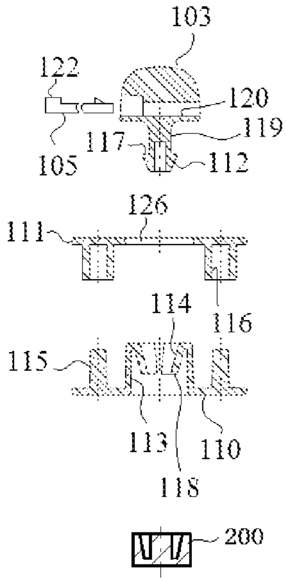

FIG. 7A is an anchored end assembled status of the snap fastener as shown in FIG. 6.

Figure 7B:
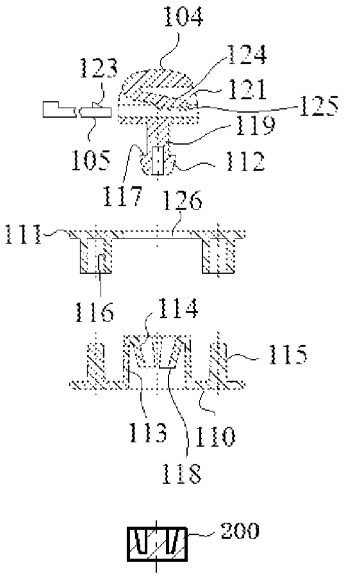

FIG. 7B is an engaging end assembled status of the snap fastener as shown in FIG. 6.

Figure 8:
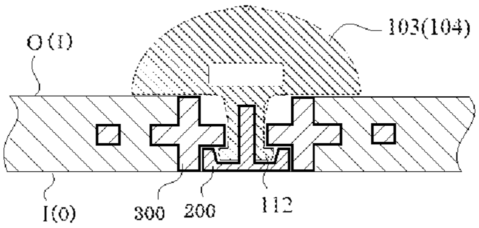

FIG. 8 is a schematic view of a snap fastener of the arm external fixing brace according to another embodiment of the present invention.

Figure 9A:
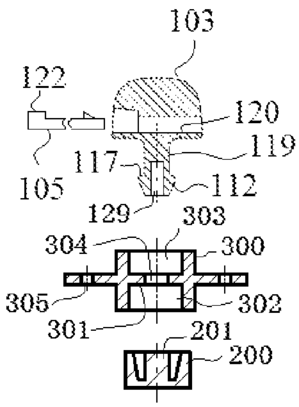

FIG. 9A is an anchored end assembled status of the snap fastener as shown in FIG. 8.

Figure 9B:
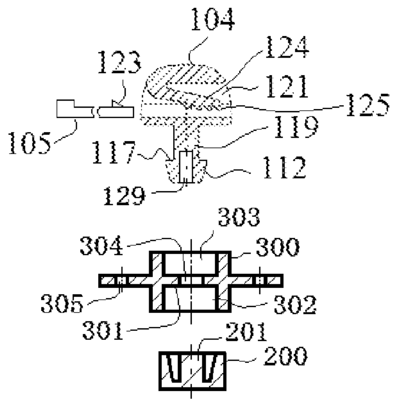

FIG. 9B is an engaging end assembled status of the snap fastener as shown in FIG. 8.

BEST MODES FOR CARRYING OUT THE PRESENT INVENTION

The invention provides a formula for a raw material of a mesh plate of an arm external fixing brace, which has less components, but can simultaneously realize some contradictory objects, i.e., preventing any adhesion in a molding process, thus facilitating removal of a prototype from a mold, making a convenient clinical operation (low temperature thermoplastic characteristics, enough ductility, and no adhesion during a clinical use), and having a wearing amenity, etc.

According to one embodiment of the invention, the formula by weight is: 60-78% of PCL (polycaprolactone); 20-38% of EVA (ethylene vinyl acetate copolymer); and 2-20% of inorganic filler (such as talc, calcium carbonate, silicate, etc.).

TABLE 1

Test Results: Proportion of all Components (weight %) in the Formula

| Component | Experimentation No. 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PCL | 78 | 65 | 60 | 50 | 30 | 50 | 50 | 60 | 78 | 40 | 50 | 60 | 65 | 75 |
| EVA | 20 | 27 | 30 | 0 | 20 | 14 | 0 | 40 | 22 | 0 | 0 | 0 | 0 | 0 |
| PP | 0 | 0 | 0 | 14 | 14 | 0 | 14 | 0 | 0 | 40 | 5 | 15 | 20 | 10 |
| PC | 0 | 0 | 0 | 0 | 0 | 0 | 0 | 0 | 0 | 0 | 25 | 10 | 0 | 5 |
| Grafting PP | 0 | 0 | 0 | 0 | 0 | 0 | 0 | 0 | 0 | 5 | 0 | 5 | 4 | 2 |
| Inorganic filler | 2 | 8 | 10 | 35 | 35 | 35 | 35 | 0 | 0 | 14 | 19 | 9 | 10 | 7 |
| crosslinking agent | 0 | 0 | 0 | 1 | 1 | 1 | 1 | 0 | 0 | 1 | 1 | 1 | 1 | 1 |

Performance Testing

At 180° C., test raw materials are put into an internal mixer according to a formula for melting modification. The modified raw materials are pressed into a 5 mm thick plate, then are cut into samples with a required size. At room temperature (25° C.±5, relative humidity ≥50%), an experimentation is performed as follows:

Method for Measuring a Tensile Ratio:

Making a strip of 5 mm×10 mm×50 mm (thickness×width×length), fixing up to 10 mm at both ends, putting into 70° C. water and heating it therein for 1 minute, taking it out, cooling it at room temperature for 20 seconds, stretching it horizontally with 20N force until its fracture incurs, measuring its tensile length, then calculating a tensile ratio.

Methods for Determining a Folding Strength:

Making a strip of 5 mm×10 mm×100 mm (thickness× width×length), fixing up to 10 mm at two ends thereof, keeping 80 mm for a free deformation between the two ends, and folding the test object upward and downward with respect to a horizontal direction up to 130°, until it cracks, recording times for folding the test object before its cracking, and calculating a folding strength.

Method for Testing a Uniformity:

Observing cut sections of the strip as the test object under a 1000X microscope, in which all components shall be evenly distributed without visible organic particles.

Product Stickiness:

Making a strip of 5 mm×10 mm×50 mm (thickness× width×length), putting it into 70° C. water and heating it therein for 1 minute, taking it out, wiping off any water, overlapping 50% of a surface of 10 mm×50 mm (width× length) and sticking an overlapped portion to each other, cooling the same, and adding 5N external force. In this case, the overlapped and sticked portions shall not be taken apart from each other. (The period from taking out the sample to bonding the sample is more than 15 seconds but less than 20 seconds)

Method for Testing a Tensile Resilience of Product:

Making a strip of 5 mm×10 mm×50 mm (thickness× width×length), fixing up to 10 mm at both ends thereof and leaving 30 mm for stretching between the two ends, stretching up to 65 mm (length) in a horizontal direction, removing an external force, waiting for the sample to retract naturally, measuring a retracted length of the sample, and calculating the sample resilience. (Resilience=S/65×100%, where S=retraction length. If S<5%, the resilience is none; if S<10%, the resilience is slight; if S<20%, the resilience is strong; and if S≥20%, the resilience is very strong)

Method for Measuring Injection Molding Quality:

Injecting modified raw materials to form a sample according to injection molding quality standards of the invention. That is, 1) placing the sample under a 10× magnifying glass to observe whether there are any particles on surfaces of the sample; and 2) visually checking whether there are pits on surfaces of the sample resulted from shrinking.

Injection Molding Conditions and Methods:

The injection molding for modified raw materials according to the present invention is quite different from those for well-known polymer materials. In the present invention, there are taken advantage of a low temperature, high pressure, slow feeding and multi-point injection to solve the problem of injection molding and mass production according to the formula. The injection molding is set as the following data: 1) a sol temperature is set at 80-160° C.; 2) an injection pressure is in a range of 40-150 MPa; and 3) an injecting rate is in a range of 2-25 g/s.

TABLE 2

Test Results

| | Experimentation No. | | | | | | | | | |
|---|---|---|---|---|---|---|---|---|---|---|
| Observing Items | 1-3 | 4 | 5 | 6 | 7 | 8 | 9 | 10-11 | 12-13 | 14 |
| Tensile ratio | ≥30% | <15% | <10% | <15% | <10% | ≥30% | | <15% | <20% | ≥30% |
| Folding Times | ≥50 | <5 | <10 | <5 | 3 | ≥50 | | <5 | | |
| Uniformity | good | bad | | | | good | | bad | | |
| Injection molding quality | Good surface | There are granules | | | | Sticking die (difficult to form), shrinkage pits appear on surfaces of product | | There are granules | | |
| Product engaging stickiness | good | N/A | | | | Very good | | N/A | good | |
| Tensile resilience of the product | small | N/A | | | | excellent | small | N/A | | |

Experimentations Nos. 1-14 show such test results that when PCL content is <50%, a tensile rate of the product is <15%; as a decomposition temperature of PCL is 180-220° C., while a melting temperature of PP and PC is >200° C., a decomposition temperature range of PCL overlaps with that of PP and PC, therefore, when PP and PC are blended together to be modified, if the PCL and PC are blended to modify at the decomposition temperature of PCL, the products would have non-melting PP and PC particles, lowering product performance; when a content of inorganic filler is >30%, a tensile property of the product is poor and it is easy to break, and if only PCL and EVA are melted together for modification, shrinkage pits appear during injection molding, resulting in a poor appearance of the product; and when EVA content is >40%, a resilience rate of the product increases, causing a poor product shaping. Therefore, if the PCL content is 60-78%, the EVA content is 20-38%, and the inorganic filler content is 2-20%, the best product quality can be made by injection molding.

According to an embodiment of the invention, FIG. 1A shows an arm external fixing brace 10, its shape memory mesh plate 12 is formed by a one-time molding process, and is arranged with a series of irregular-shaped large holes 11. A thickness of edges of the mesh plate 12 is greater than that of the central area thereof, while a thickness of an edge of each large hole 11 is less than a thickness of a rib, a bridging portion, between two adjacent large holes 11.

Figure 1B:
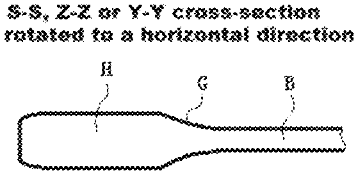
FIGS. 1B-1C are schematic views of sections S-S, X-X, Z-Z and Y-Y of the arm external fixing brace as shown in FIG. 1A, showing a thickness therein.

FIG. 1B shows a local thickness at an upper edge S-S, a left edge Z-Z and a right edge Y-Y of the mesh plate 12. A thickness H at an edge of the mesh plate is greater, while a thickness B at a central area of the mesh plate is smaller, and a thickness G from the edge of the mesh plate to the center portion of the mesh plate gradually decreases.

Figure 1C:
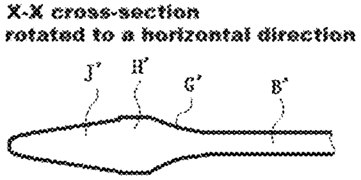

FIG. 1C shows a local thickness variation at a bottom edge X-X of the mesh plate 12, in which a thickness H' at the edge of the mesh plate is greater, while a thickness B' at the central area of the mesh plate is smaller; and on the edge of the mesh plate, the closer to a center of the mesh plate, the smaller thickness G'. In particular, the closer the edge of the mesh plate, the smaller the thickness J'.

As shown in FIGS. 1A, 2*a* and 2*b*, the irregular-shaped large hole 11 has a transition arc 13, the minimum transition radius is 0.5 mm, and the minimum transition fillet is 10 degrees.

A span B is at least greater than the thickness t, preferably less than 50 times of the thickness, more preferably less than 30 times of the thickness.

A ratio of the maximum span L to the minimum span B is 1:1 to 40:1, preferably 1:1 to 30:1, more preferably 1:1 to 20:1.

A width b of the rib between two large holes 11 is at least greater than the maximum thickness of the rib between the two large holes 11, preferably greater than 1.5× the maximum thickness of the rib between the two large holes 11, more preferably greater than 2 times of the maximum thickness of the rib between the two large holes 11.

A total area of the all large holes 11 is 25-98% of an area of the shape memory mesh plate 12, preferably 27-80%, more preferably 29-60%, most preferably 30-55%.

The maximum thickness of the shape memory mesh plate 12 is at least 3 mm, preferably 4-6 mm, more preferably 5 mm. In particular, a thickness of a portion 14 facing to a convex wrist bone designed to be thinner than that of other portions; and a hole 15 with a special shape is reserved at a local area corresponding to a thumb. According to actual needs, the special shaped hole 15 can be a peach shaped, an oblong, and a substantial triangular, etc.

An adjustable external fixing brace 10 as shown in FIG. 1A is used for fixing a patient's arm to make its rehabilitation. In other embodiments, the present invention is also applicable to a human bone rehabilitation by fixing fractures of limbs, chest, neck, waist, hand, foot or other parts of a human body.

With respect to a longitudinal axis of the adjustable external fixing brace 10, near the two sides thereof, there are provided with a plurality of snap fasteners as anchored or engaging terminals of a connecting means 16, which can be inserted into, installed within, or bonded to the shape memory mesh plate 12, or can be integrated with the shape memory mesh plate 12. A height of the snap fastener 16 may be substantially the same as a thickness of the shape memory mesh plate 12 at which it is located.

Figure 3A:
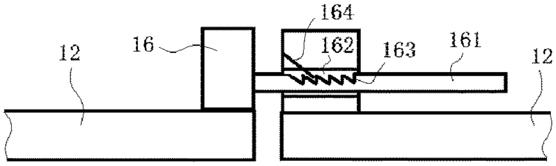

In the embodiment as shown in FIG. 3*a*, a connecting means 16 may be a buckle structure, and the connecting means 16 mounted on one side of the shape memory mesh plate 12 is provided with a check belt 161, which has several straight teeth 163; while on the other side of the shape memory mesh plate 12, the connecting means 16 is provided with a pass through groove 162 and a check rod 164 of the check belt 161. When the check rod 164 contacts with a straight tooth 163, the check belt 161 cannot be withdrawn, so as to facilitate locking the connecting means 16; however, whenever the check rod 164 is manually turned to aside, the check belt 161 can be restored to a free extracting state to facilitate the release the connecting means 16.

Figure 3B:
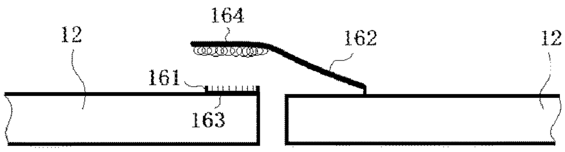

In the embodiment as shown in FIG. 3*b*, a connecting means 16 can be a nylon tape structure. The connecting means 16 installed on one side of the shape memory mesh plate 12 is provided with a nylon seat 161 on which there is a lot of nylon velvet 163; while on the other side of the shape memory mesh plate 12, the connecting means 16 is provided with a nylon belt 162, on which a lot of nylon rings 164 are arranged. When the nylon piles 163 and the nylon rings 164 are attached with each other, the connecting means 16 is locked; however, whenever the nylon rings 164 are pulled up manually, the connecting means 16 can be released.

Figure 3C:
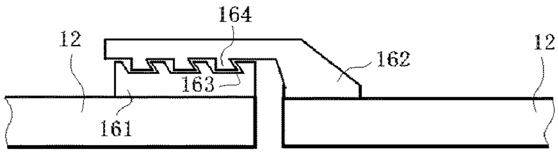

In the embodiment as shown in FIG. 3*c*, a connecting means 16 can be a toggle structure, and on one side of the shape memory mesh plate 12, the connecting means 16 is provided with a toggle seat 161, on which there are teeth 163 with barbs; while on the other side of the shape memory mesh plate 12, the connecting means 16 is provided with a hinged cover 162, on which at least one a hook 164 are arranged. When the hooks 164 are hooked on the teeth 163, the connecting means 16 is locked; however, the connecting means 16 can be released when the hinged cover 162 is pulled up manually.

Figure 3D:
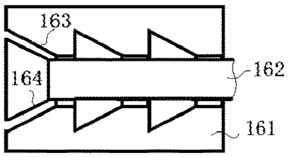

In the embodiment as shown in FIG. 3*d*, a connecting means 16 may be mortise structure, and on one side of the shape memory mesh plate 12, the connecting means 16 is provided with a row of trapezoidal slots 163 which are as female connecting parts 161; while on the other side of the shape memory mesh plate 12, the connecting means 16 is provided with a trapezoid head 164 which is a male connecting part 162. When the trapezoid head 164 is embedded into one of trapezoid slots 163, the connecting means 16 is locked; however, when the trapezoid head 164 is manually pulled out, the connecting means 16 can be relaxed.

Figure 3E:
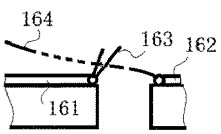

In the embodiment as shown in FIG. 3*e*, a connecting means 16 can be a belt type structure, having a fixing pin and several holes. On one side of the shape memory mesh plate 12, the connecting means 16 is provided with an anchored end 161 on which there is a belt fixing pin 163, while on the other side of the shape memory mesh plate 12, the connecting means 16 is provided with a belt fixing pin receiving end 162, on which a series of holes 164 are arranged. When the fixing pin 163 is inserted into one hole 164, the connecting means 16 is locked; however, when the fixed pin 163 is manually moved away from the hole 164, the connecting means 16 can be released.

According to the arm external fixing brace, the shape memory mesh plate is provided with large holes everywhere, is made by a modification technology, and is made of polymer material. In hospital, the doctor firstly heats the product at 70-80° C. (or 60-70° C.) to make it become soft; after being softened, the shape memory mesh plate with large holes is reduced to a temperature of 65° C. within 15 minutes (preferably 12 minutes, more preferably 10 minutes), preferably lower than 60° C., more preferably lower than 50° C. Then, the shape memory mesh plate with large holes is enclosed to where it needs to be fixed. Further, the shape memory mesh plate with large holes is stretched and deformed, so as to make the same contact a skin of the fixed portion. At last, the two sides of the shape memory mesh plate with large holes are connected with each other.

FIG. 4 shows a thumb holding accessory 20, which has a base 2008 and a thumb holding cylinder 2009, and the base 2008 has a frustum surface 2002 and an undersurface 2003. The thumb holding cylinder 2009 has an upper wall 2004 and a lower wall 2005. A side wall 2009SW of the thumb holding cylinder 2009 is provided with at least one air hole 2007. The upper wall 2004 of the thumb holding cylinder 2009 is provided with a slit 2006 for adjusting the inner diameter as a size of a user's thumb. There is an annular connecting ring 2001 between the base 2008 and the lower wall 2005, and between the base 2008 and the upper wall 2004, which is convenient for a user to adjust the thumb holding holder 2009 to his most comfortable orientation.

In clinical use, the thumb holding cylinder 2009 is inserted into a thumb hole 15 of the mesh plate 12, to make the frustum surface 2002 of the base 2008 of the thumb holding accessory 20 closely contact the cone surface 1202 of the edge of the thumb hole 15 of the mesh plate 12, making a gap 1204 between the base 2008 and the edge of the thumb hole 15 disappear, in this case, the undersurface 2003 of the thumb holding accessory 20 is flush with a surface 1201 of the mesh plate 12, so as to make the patient comfortable and his/her thumb blood flow smoothly, and prevent any local ulceration at a thumb root.

The cone surface 1202 on one side of the thumb hole 15 of the mesh plate 12 is symmetrical with the cone surface 1203 on the other side thereof, so that the mesh plate 12 can be used for both the left arm and the right arm, and the thumb holding cylinder 2009 can be used for both the left thumb and the right thumb. Therefore, according to the present invention, one type of product can be used for multi-purposes, make it possible to reduce numbers of product types, increase amount for each of types, and reduce a cost for producing each of types of products.

According to the embodiment as shown in FIG. 5, a plurality of snap assembling means 101 and 102 are installed on both sides of a mesh plate assembly 100 adjacent to two transverse edges respectively. The snap assembling means 101 and 102 are provided with an anchored end 103 of a connecting band 105 and an engaging end 104 of the connecting band 105. The anchored end 104 and the engaging end 104 are rotatably mounted on the mesh plate assembly 100, respectively. In clinical use, the mesh plate assembly 100 is shaped so that an inner surface I thereof surrounds a wound of the patient. On an outer surface O, an anchor head 106 of the connecting band 105 is fixed in the anchored end 103, and the engagement head 107 is fixed in the engaging end 104, thus making the two transverse edges of the mesh plate assembly 100 connected to each other.

FIG. 6 is a partially enlarged schematic view of positioning and mounting mechanism of the snap assembling means 101 and 102. FIG. 7A-7B are explosive view of the positioning and mounting of the snap assembling means 101 and 102.

As shown in FIGS. 5-6, 7A and 7B, according to an embodiment of the present invention, a mesh plate assembly 100 with several large air holes is injection molded by a shape memory material. On both surfaces O and I of each side of the mesh plate assembly 100 adjacent to the transverse edge, a plurality of mounting concaves 99 and 98 for receiving the snap assembling means 101 and 102 are symmetrically arranged, or a plurality of the mounting concaves 99 and 98 for containing the snap assembling means are arranged on at least one side of the mesh plate assembly. At the mounting concaves 99 and 98, a thickness of the mesh plate assembly 100 becomes thinner. The mounting concaves 99 and 98 are provided to contain parts 111 and 110 for mounting the snap assembling means.

The snap assembling means 101 and 102 are provided with a buckle fixing seat 111 and a buckle connecting pin 119. The buckle fixing seat 111 is arranged opposite to the mounting concave 98 on one side surface I of the mesh plate assembly 100, while the buckle connecting pin 119 is rotatably and nonreturnably inserted into the buckle fixing seat 111 from the other side surface O of the mesh plate assembly 100.

The buckle fixing seat 111 is in engagement with a check cylinder 114 with elastically expanding diameter, and the buckle connecting pin 119 is provided with a check head 112 which has a check surface 117. After the check head 112 passes through the check cylinder 114, the check cylinder 114 retracts elastically along its radial direction, so that an end face 118 of the check cylinder 114 contacts the check surface 114 of the check head 112. However, the buckle connecting pin 119 can rotate freely within 360 degrees within the check cylinder 114.

The buckle connecting pin 119 is also provided with a head 103 or 104, and the head is provided with a channel 120 or 121, which is used for a channel of ahead end 122 of the connecting band 105 or a channel of an engaging end 123 of the connecting band 105.

The channel used for the head end 122 of the connecting band 105 is a square hole with a step in it, and the channel used for the engaging end 123 of the connecting band 105 is provided with a stopping tongue 124, preferably, the stopping tongue 124 is provided with a stopping tooth 125.

The check cylinder 114 is arranged in a center of a buckle fixing seat 110, the buckle fixing seat 110 includes a substrate, and the check cylinder 114 is arranged in a center of the substrate and is perpendicular to the substrate. Preferably, a side wall of the check cylinder 114 is provided with at least one slit along its generatrix.

A guiding sleeve or guiding rod 115 perpendicular to the substrate is symmetrically arranged on both sides of the substrate with respect to a longitudinal direction of the check cylinder 114.

The buckle fixing seat 111 is also a snap cover, a center of the snap cover 111 is provided with a central hole 126 engaged with an outer surface of the check cylinder 114. On two sides of the central hole 126, there are symmetrically provided with a guiding rod or a guiding sleeve 116 perpendicular to the snap cover 111. The guiding rod or the guiding sleeve 116 is in engagement with the guiding sleeve or the guiding rod 115.

Along a longitudinal direction of the substrate, a thickness of the substrate on an outside of the guiding sleeve or guiding rod 115 is not greater than a thickness of the substrate between the two guiding sleeves or guiding rods 115. An outer diameter of one end of the check cylinder 114 away from the substrate is not less than an outer diameter of the other end of the check tube 114 adjacent to the substrate. The check cylinder 114 is connected with the substrate by a support cylinder 113, and an angle between an outer wall of the check cylinder 114 and an inner wall of the supporting cylinder 113 is a sharp angle.

A sum of a height of the check cylinder 114 and a height of the check head 112 is less than a height of the support cylinder 113. A center column of a flush surface making plug 200 is inserted into a center hole of the check head 112 with multiple longitudinal slits, to push circumferential hooks of the check head 112 radially outward, so as to improve the check reliability. Meanwhile, the flush surface making plug 200 and the buckle fixing seat 110 are flush with the inner surface I of the mesh plate assembly 100.

As shown in FIGS. 8, 9A and 9B, according to another embodiment of the invention, during a mesh plate assembly 100 with large air holes is injection molded with a shape memory material, a plurality of snap assembling substrates 300 are embedded at the same time. During an injection molding of the mesh plate 12, the injection molding material is poured into side holes 305 at the two wings of the snap assembling substrates 300, so that the snap assembling substrates 300 and the mesh plate 12 are integrated. On the two surfaces of a center portion of the snap assembling substrate 300, there are symmetrically provided with concaves 302 and 303. In this way, if the mesh plate 12 is used to fix a left arm, then the concave 302 is used to assembly a snap fastener, while if the mesh plate 12 is used to fix a right arm, then the concave groove 303 is used to assembly a snap fastener.

Preferably, the concaves 302 and 303 are non-circular, such as oblong, square and D-shaped, so as to prevent any rotary displacement of a corresponding shape plug 200 within the concaves 302 and 303.

A central hole 304 is arranged in a center of the snap assembling substrate 300. Check surfaces 301 are arranged on both sides of the substrate within the concaves 302 and 303.

A side wall of the buckle connecting column 119 are provided with at least one slit along its generatrix, and at end of the side wall, there is provided with a check head 112 which has a check surface 117. After the check head 112 passes through the snap fastener substrate 300, the check surface 117 of the check head 112 is clamped on the check surface 301.

A central column 201 of a flush making plug 200 is inserted into a central hole 129 of the check head 112 with a plurality of longitudinal slits, to put circumferential hooks of the check head 112 radially outward, so as to improve the check reliability. At the same time, the flush making plug 200 is flush with the inner surface I of the mesh plate 12.

According to the arm external fixing brace of the invention, the large holes are arranged on the mesh plate, making it convenient to directly watch any updating wound and prevent any occurrence of post-traumatic complications; making it to meet fresh air; making the user's wet skin quick drying after shower; making it to improve skin hygiene of patients and prevent from incurring pruritus and dermatitis; and making it to have a light weight.

The arm external fixing brace according to the invention, there is an easily detachable and adjustable connecting means, which can adjust a clamping tightness throughout a course of arm swelling of the patient, maintain a soft tissue compression, and has a good fixation effect.

According to the invention, there is used a thermoplastic memory material which has a good extensibility, and can deform at any angle and in any direction. In particular, the mesh structure has a better extensibility and can be applied for fat or thin users (patients with different body types). Therefore, with the present invention, a number of kinds of products can be reduced, a cost for making any type of product can be reduced, and a number of types of products which hospitals have to purchase are also reduced.

According to the present invention, the mesh plate with large holes is made by a one-time injection molding, which has no drilling process, no waste and leftover materials, no coating process, and no sticking even when no longer coating the product, and which has a high production efficiency, and a low manufacturing cost.

According to the present invention, the mesh plate takes advantage of a thermoplastic material which has a good processing performance (injection molding), a good ductility, and is not adhesive, and which can be injection molded into a fixing brace for different human parts (hands, limbs, neck, chest, waist or feet).

According to the present invention, the mesh plate has large holes, which are convenient for meeting fresh air; the external fixing brace can be composed of one or more pieces, and can be equipped with different snap assembling means; on special parts of the mesh plate, a large hole pattern and a local thickness can be different (such as a thickness of the mesh plate corresponding to ulnar styloid, ankle, etc. is less than or equal to a thickness of other parts thereof).

According to the present invention, the fixing brace can be formed by arbitrary stretching and deforming to have a different shape or angle according to a profile where a human body is injured with fracture; it is not necessary to cut the mesh plate to fit any individual patient; the product itself is not sticky; except for the snap assembling means, the mesh plate is composed of the same chemical material, and the surface thereof does not need to be coated or impregnated with other substances; after being connected by a connecting means, an irregular cylinder shape suitable for wounded body shape can be formed; it can fix all parts of human body, such as neck, chest, limbs and so on; according to an update swelling of an area of fracture, a tightening degree of the fixing brace can be adjusted more or less; it is convenient to dismantle, and it is easy to treat and nurse an injured part; and the mesh plate itself does not absorb water, and the patient wearing the mesh plate can take a bath.

The present invention overcomes a bias in prior art, a prejudice of traditional technology, does not respect the traditional technology, nor is restricted by traditional material selection, but boldly develops a new product with innovations, selects a new material, a new process, a new type and a new product structure, and provides a mesh plate which has a lower manufacturing cost, a simpler manufacturing process, a more convenient medical use, and is a safer and more comfortable for patients to wear, and more suitable for fracture rehabilitation of patients according to a human anatomical structure.

According to the present invention, the connecting column itself can rotate freely at the anchored end and the engaging end of the snap assembling means. In clinical use, no matter how the mesh plate is stretched, the corresponding two anchored end and engaging ends can be adjusted and completely aligned with each other through adaptive steering, making the external fixing brace easy to be connected and adjustable.

According to the present invention, the mesh plate with large holes, as a medical fixing brace, no longer needs to prepare one type for left arm or leg foot and the other type for right arm and leg foot, respectively, realizing a universal brace blank for both the left and right arm, both the left and right leg, and both the left and right foot, and can increase an amount of any type of the market available mesh plate, and further reduce the cost and facilitate clinical use.

The above description clearly discloses all aspects of the concept of the present invention. According to the disclosed embodiments, those skill in the art can make various improvements, substitutions, supplements, modifications, variations, amendments, etc. for the present invention, however, all of these will fall into the scope of protection of the present invention as defined in the appended claims.

The invention claimed is:

1. An arm external fixing brace, wherein a thickness of edges of a mesh plate is greater than a thickness of a central portion thereof;

there is provided with a thumb holding accessory (20), which has a base (2008) and a thumb holding cylinder (2009), and the base has a frustum (2002) and an undersurface (2003); an upper wall (2004) of the thumb holding cylinder (2009) is provided with at least one longitudinal slit (2006); a side wall (2009SW) of the thumb holding cylinder (2009) is provided with at least one air hole (2007); and a ring (2001) with a reduced thickness connects the thumb holding cylinder (2009) to the base (2008);

the thumb holding cylinder (2009) is inserted into a thumb hole (15) of the mesh plate (12), so that a frustum surface (2002) of the base (2008) of the thumb holding accessory (20) abuts a cone surface (1202) of a thumb hole edge of the mesh plate (12), making a gap (1204)

between the base (2008) and the thumb hole edge disappear, so that the undersurface (2003) of the thumb holding accessory (20) is flush with a skin contacting surface (1201) of the mesh plate (12).

2. The arm external fixing brace according to claim 1, wherein two wings of each of a plurality of snap fastener substrates are provided with a side hole; in a central portion of each of the plurality of snap fastener substrates, there are symmetrically provided with a concave on an up surface and a concave on a down surface, respectively; each of the plurality of snap fastener substrates is provided with a center hole, and a check surface is each formed around the center hole in the concave on the up surface and the concave on the down surface.

3. The arm external fixing brace according to claim 2, wherein the concave on the up surface and the concave on the down surface is non-circular.

4. The arm external fixing brace according to claim 3, wherein the concave on the up surface and the concave on the down surface is any blind opening with at least one straight edge.

5. The arm external fixing brace according to claim 3, wherein the concave on the up surface and the concave on the down surface is an oblong, a square or a D-shaped.

6. The arm external fixing brace according to claim 1, wherein the thumb holding accessory (20) has a largest size of 72 mm, a medium size of 64 mm, or a smallest size of 56 mm; a length tolerance of the thumb holding accessory (20) is ±7 mm, a thickness tolerance of the thumb holding accessory (20) is ±2 mm; the base (2008) is oblong with a 72 mm length and a 56 mm width.

7. The arm external fixing brace according to claim 6, wherein the base (2008) has a thickness of 1 mm.

8. The arm external fixing brace according to claim 1, wherein the arm external fixing brace is made by a low temperature, high pressure, slow feeding, and multi-point injection molding method.

9. The arm external fixing brace according to claim 1, wherein the arm external fixing brace comprises 60-78 weight % of PCL; 20-38 weight % of EVA; and 2-20 weight % of an inorganic filler.

10. The arm external fixing brace according to claim 9, wherein the inorganic filler comprises talc powder, calcium carbonate, or silicate.

* * * * *